(12) United States Patent
Krishna (10) Patent No.: US 8,415,337 B1
(45) Date of Patent: Apr. 9, 2013

(54) IBUPROFEN COMPOSITIONS AND METHODS OF MAKING SAME

(75) Inventor: Aravind Krishna, Skillman, NJ (US)

(73) Assignee: Recordati Rare Diseases Inc., Lebanon, NJ (US)

( * ) Notice: Subject to any disclaimer, the term of this patent is extended or adjusted under 35 U.S.C. 154(b) by 0 days.

(21) Appl. No.: 13/410,989

(22) Filed: Mar. 2, 2012

Related U.S. Application Data (60) Provisional application No. 61/449,692, filed on Mar. 6, 2011.

(51) Int. Cl.
*A01N 43/00* (2006.01)

(52) U.S. Cl.
USPC ........................................................ 514/183

(58) Field of Classification Search .................... 514/183
See application file for complete search history.

(56) References Cited

U.S. PATENT DOCUMENTS

| | | | |
|---|---|---|---|
| 4,145,440 A | 3/1979 | Fitch et al. | |
| 4,279,926 A | 7/1981 | Bruzzese et al. | |
| 5,895,789 A | 4/1999 | Gentile et al. | |
| 6,342,530 B1 | 1/2002 | Darko | |

FOREIGN PATENT DOCUMENTS

| | | |
|---|---|---|
| CN | 102180785 A | 9/2011 |

OTHER PUBLICATIONS

Zadora G. 2009, Classification of Glass Fragments Based on Elemental Composition and Refractive Index, J Forensic Sci., 54(1):49-59.
Press Release, Jul. 30, 2010, Lundbeck Inc. Announces the voluntary Nationwide Recall of Two Lots of NeoProfen (ibuprofen lysine) injection, http://www.lundbeck.com/us/media/press-releases/2010/lundbeck-inc-announces-the-voluntary-nationwide-recall-of-two-lots-of-neoprofen-ibuprofen-lysine-injection.
Aug. 8, 2010, NeoProfen (ibprofen lysine) Injection: Recall and Shortage—Risk of Particulate Matter, http://wwwfda.gov/Safety/Medwatch/SafetyInformation/safetyalertsforhumanmedicalproducts/ucm220798.htm.
Oct. 2009, "Special Solutions", SHOTT forma vitrum.
May 2009, "Daikyo Technical Report Characteristics of Daikyo Resin CZ," Daikyo Seiko, DS-CZ-E012.
Baydoun L et al., 2004, "Comparison of different ibuprofen-amino acid compounds with respect to emulsifying and cytotoxic properties", International Journal of Pharmaceutics, 274:157-165.
Libiao, L. et al, 1994, "Preparation of Ibuprofen Lysine and Its injection", Journal of China Pharmaceutical University, 25 (2):80-82.
Woertz, K. et al, 2011, "A Comparative study on two electronic tongues for pharmaceutical formulation development". Journal of Pharmaceutical and Biomedical Analysis. 55:272-281.
Zgoda, M. et al., 2007, "Viscosity of hydrogel pharmaceutical products and the rate of diffusion of ibuprofen hydrotropic binding through model phase boundary in vitro", Polymers in Medicine, T.XXXVII.(1):1-11.

*Primary Examiner* — Brandon Fetterolf
*Assistant Examiner* — Jean Cornet
(74) *Attorney, Agent, or Firm* — Stephen G. Kalinchak; Margaret M. Buck (57) ABSTRACT

The present invention provides an improved ibuprofen lysine pharmaceutical composition and a process for preparing the same.

10 Claims, 5 Drawing Sheets

Figure 1. FTIR Spectrum of Particulate Matter from Ibuprofen Lysine in Wheaton Type I vials Stored at 60°C for 2 weeks Figure 2. FTIR Spectrum of Ibuprofen Aluminum Salt Figure 3. FTIR Spectrum of Particulate Matter from Ibuprofen Lysine in Wheaton Type I vials Stored at 60°C for 3 weeks Figure 4. SEM Micrograph of Schott 2R Type I Plus Vial. Interior Surface, 200X Figure 5. SEM Micrograph of Wheaton Vial. Interior Surface, Area 2, 200X

IBUPROFEN COMPOSITIONS AND METHODS OF MAKING SAME

CROSS-REFERENCE TO RELATED APPLICATION

The present application is a U.S. Nonprovisional Patent Application claiming the benefit of U.S. Provisional Applications No. 61/449,692, filed Mar. 6, 2011, which is herein incorporated by reference in its entirety.

FIELD OF THE INVENTION

This invention relates to improved pharmaceutical compositions of alkylammonium salts of ibuprofen, such as ibuprofen lysinate, and processes for preparing the pharmaceutical compositions.

BACKGROUND OF THE INVENTION

Ibuprofen is a phenylpropionate or 2-arylpropionic acid also known as 2-[4-(2-methylpropyl)phenyl]propanoic acid.

U.S. Pat. No. 4,279,926 (Bruzzese et al.) discloses pharmaceutical compositions containing salts of phenylalkanoic acids, including the D,L and L lysine salts of ibuprofen and is directed to methods of treating inflammation and pain using the same.

U.S. Pat. No. 5,895,789 (Gentile et al) is directed to pharmaceutical compositions suitable for parenteral administration that contain an alkylammonium salt of a 2-arylpropionic acid, include an aqueous solution having an osmolarity between 270 and 310 mOsm/kg and a pH in the range of 7.0 to 7.5, are free of preservatives and of supporting substances and prepared and kept in an inert gas atmosphere and away from light, as well as a process for preparing these pharmaceutical compositions.

U.S. Pat. No. 6,342,530 (L. Darko) is directed to pharmaceutical compositions in unit dosage form in a vial or ampoule having storage stability over a period of 2 years and suitable for parenteral administration having anti-inflammatory, anti-pyretic and analgesic properties, which consists of a therapeutically effective amount of the d,l or l-lysine salt of R,S or S-ibuprofen as active ingredient dissolved in sterile water to form a solution in the absence of an inert atmosphere and substantially free of any excipient, organic solvent, buffer, acid, base, salt other than the active ingredient and capable of storage in the absence of an inert atmosphere.

Surprisingly it now has been found that an ibuprofen aluminum salt precipitate can form in these pharmaceutical compositions. The presence of the ibuprofen aluminum salt precipitate may result in the ibuprofen alkylammonium salt pharmaceutical composition being unsuitable for therapeutic use. An alkylammonium salt ibuprofen pharmaceutical composition that is substantially-free of an ibuprofen aluminum salt precipitate would be beneficial since the therapeutic use of the pharmaceutical composition would not be compromised. The present invention is directed to these, and other important, ends.

SUMMARY OF THE INVENTION

The present invention provides a pharmaceutical composition comprising:
  a) an alkylammonium salt of R-ibuprofen, S-ibuprofen or R,S-ibuprofen that is capable of complexing with aluminum; and
  b) an aqueous or a non-aqueous solvent; wherein:
the composition is:
  c) in unit dosage form in an environment for keeping;
  d) preservative-free or in a presence of an excipient; and
  e) substantially-free of ibuprofen aluminum salt precipitate.

The present invention also provides a pharmaceutical composition comprising:
  a) an an alkylammonium salt of ibuprofen selected from the group consisting of R-ibuprofen, S-Ibuprofen and R,S-ibuprofen that is capable of complexing with aluminum; and
  b) an aqueous or a non-aqueous solvent; wherein:
the composition is in a unit dosage form in an environment for keeping comprising:
  c) optionally an absence of preservative;
  d) optionally a presence of an excipient; and
  e) a substantial absence of ibuprofen aluminum salt precipitate.

The present invention also provides a pharmaceutical composition comprising:
  a) an an alkylammonium salt of ibuprofen selected from the group consisting of R-ibuprofen, S-Ibuprofen and R,S-ibuprofen that is capable of complexing with aluminum;
  b) an aqueous or a non-aqueous solvent;
  c) optionally an absence of a preservative;
  d) optionally a presence of excipient; and
  e) a substantial absence of ibuprofen aluminum salt precipitate;
  wherein the composition is in a unit dosage form in an environment for keeping.

The invention also provides a process for the preparation of the pharmaceutical composition of the invention, the process comprising:
  (a) mixing an alkylammonium salt of R-ibuprofen, S-ibuprofen or, S-ibuprofen that is capable of complexing with aluminum with an aqueous or a non-aqueous solvent;
  (b) optionally adjusting the pH of mixture (a) to about 7.0 with sodium hydroxide or hydrochloric acid;
  (c) filtering mixture (a) or (b) as the case may be;
  (d) aseptically processing filtered mixture (c) while placing it in an environment for keeping;
  (e) sealing the environment for keeping; and
  (f) optionally terminally sterilizing.

The invention also provides a pharmaceutical composition comprising:
  (a) an alkylammonium salt of R-ibuprofen, S-ibuprofen or R,S-ibuprofen that is capable of complexing with aluminum; and
  (b) an aqueous or a non-aqueous solvent; wherein:
the composition is:
  (a) in unit dosage form in an environment for keeping;
  (b) preservative-free or in a presence of an excipient; and (c) substantially-free of ibuprofen aluminum salt precipitate;

prepared by a process comprising the steps:
(a) mixing an alkylammonium salt of R-ibuprofen, S-ibuprofen or R,S-ibuprofen that is capable of complexing with aluminum compounds with an aqueous solution, suspension or emulsion, or a non-aqueous solution, suspension or emulsion;
(b) optionally adjusting the pH of mixture (a) to about 7.0 with sodium hydroxide or hydrochloric acid;
(c) filtering mixture (a) or (b) as the case may be;
(d) aseptically processing filtered mixture (c) while placing it in an environment for keeping;
(e) sealing the environment for keeping; and
(f) optionally terminally sterilizing.

The invention also provides a pharmaceutical composition comprising:
a) an an alkylammonium salt of ibuprofen selected from the group consisting of R-ibuprofen, S-Ibuprofen and R,S-ibuprofen that is capable of complexing with aluminum;
b) an aqueous or a non-aqueous solvent;
c) optionally an absence of a preservative;
d) optionally a presence of excipient; and
e) a substantial absence of ibuprofen aluminum salt precipitate;

wherein the composition is in a unit dosage form in an environment for keeping;
prepared by a process comprising the steps:
f) mixing an alkylammonium salt of R-ibuprofen, S-ibuprofen or R,S-ibuprofen that is capable of complexing with aluminum compounds with an aqueous solution, suspension or emulsion, or a non-aqueous solution, suspension or emulsion;
g) optionally adjusting the pH of mixture (a) to about 7.0 with sodium hydroxide or hydrochloric acid;
h) filtering mixture (a) or (b) as the case may be;
i) aseptically processing filtered mixture (c) while placing it in an environment for keeping;
j) sealing the environment for keeping; and
k) optionally terminally sterilizing.

DETAILED DESCRIPTION OF THE INVENTION

The invention provides a pharmaceutical composition comprising:
(a) an alkylammonium salt of R-ibuprofen, S-ibuprofen or R,S-ibuprofen that is capable of complexing with aluminum; and
(b) an aqueous, or a non-aqueous solvent; wherein:
the composition is:
(a) in unit dosage form in an environment for keeping;
(b) preservative-free or in a presence of an excipient; and
(c) substantially-free of ibuprofen aluminum salt precipitate.

The present invention also provides a pharmaceutical composition comprising:
f) an an alkylammonium salt of ibuprofen selected from the group consisting of R-ibuprofen, S-ibuprofen and R,S-ibuprofen that is capable of complexing with aluminum; and
g) an aqueous or a non-aqueous solvent; wherein:
the composition is in a unit dosage form in an environment for keeping comprising:
h) optionally an absence of preservative;
i) optionally a presence of an excipient; and
j) a substantial absence of ibuprofen aluminum salt precipitate.

The present invention also provides a pharmaceutical composition comprising:
f) an an alkylammonium salt of ibuprofen selected from the group consisting of R-ibuprofen, S-Ibuprofen and R,S-ibuprofen that is capable of complexing with aluminum;
g) an aqueous or a non-aqueous solvent;
h) optionally an absence of a preservative;
i) optionally a presence of excipient; and
j) a substantial absence of ibuprofen aluminum salt precipitate;
wherein the composition is in a unit dosage form in an environment for keeping.

Though injectable pharmaceutical compositions often contain subvisible extraneous particles (such as cellulose and elastomers) when examined under a microscope, which frequently come from container-closure components and/or manufacturing, it now surprisingly has been found that the predominant particulate in ibuprofen alkylammonium salt compositions of the prior art is an organo-aluminum salt. Without being bound by any one theory, it is possible that the salt of the ibuprofen alkylammonium salt composition extracts aluminum from the glass vial or ampoule in which the pharmaceutical composition typically is contained being that it is known that the elemental composition of glass includes aluminum (see e.g., G. Zadora, "Classification of Glass Fragments Based on Elemental Analysis and Refractive Index," *J. Forensic Sci.*, (2009) 54(1): 49-59), resulting in an aluminum-lysine complex. Further, ibuprofen of the pharmaceutical composition may extract aluminum from the glass vial or glass ampoule since it is a carboxylic acid, as well as be in equilibrium with the aluminum-lysine complex where aluminum is exchanged between the two acids.

The phrase "environment for keeping" or simply "environment" is defined herein, unless otherwise stated, as a means for containing the unit dosage form. Non-limiting examples of an environment for keeping are a vial, ampoule, blister pack, and prefillable delivery systems such as syringes and cartridges.

As used herein, the phrases "substantially-free of ibuprofen aluminum salt precipitate" and "substantial absence of ibuprofen aluminum salt precipitate" mean that the pharmaceutical composition has at least no visible or subvisible particulate matter, such as at least less than about 5 µg/L of ibuprofen aluminum salt precipitate.

In some embodiments, the alkylammonium salt is selected from a group consisting of d,l-lysine, l-lysine, d-lysine, tromethamine and meglumine. In some embodiments, the alkylammonium salt is d,l-lysine, l-lysine, or d-lysine. In some embodiments, the salt is d-lysine. In some embodiments, the salt is l-lysine.

In some embodiments, the environment for keeping is selected from a group consisting of a vial, an ampoule, a blister pack and a prefillable delivery system. In some embodiments, the environment is a vial or an ampoule. In some embodiments, it is a vial. In some embodiments, it is an ampoule. In some embodiments, it is a blister pack. In some embodiments, it is a prefillable delivery system. In some embodiments, the prefillable delivery system is a syringe or a cartridge.

The environment for keeping is comprised of a material, or combination of materials, that is inert to the complexing of any aluminum content it may have with the R-ibuprofen, S-ibuprofen or R,S-ibuprofen alkylammonium salt composition it contains.

In some embodiments, the environment for keeping is comprised of glass, such as a vial or an ampoule. In some embodiments, the aluminum content of the glass environment is negligible such that the ibuprofen salt composition in it is substantially-free of ibuprofen aluminum salt precipitate. In some embodiments, the glass environment further comprises a coating disposed on the inner wall of it that inhibits or reduces the aluminum content of it from complexing with the R-ibuprofen, S-ibuprofen or R,S-ibuprofen alkylammonium salt composition it contains. In some such embodiments, the coating is comprised of silicon dioxide, Teflon®, or any other inert material that inhibits or reduces the aluminum content of the glass environment from complexing with the R-ibuprofen, S-ibuprofen or R,S-ibuprofen alkylammonium salt composition the glass environment contains. For example, Schott Type I Plus® vials (Schott North America, Inc., Lebanon, Pa., U.S.A.), which are glass vials having an inert quartz-like non-porous coating consisting of 100% $SiO_2$ that covalently bonds to the inner surface of the vial and a thickness of 100-200 nm.

In some embodiments, the coating is silicon dioxide. In some embodiments, the coating is Teflon®. In some embodiments, the coating is an inert polymer.

In some embodiments, the environment for keeping is comprised of an inert polymeric material. For example, Dalkyo Crystal Zenith® vials and prefillable delivery systems (West Pharmaceutical Services, Lionville, Pa., U.S.A., the U.S. affiliate of Dalkyo Seiko, Ltd., Tokyo, Japan), which are comprised of a proprietary cyclic olefin polymer material.

The aqueous solvent of the pharmaceutical composition can be any grade of water suitable for parenteral applications. For example, Water for Injection, USP.

The non-aqueous solvent of the pharmaceutical composition can be ethanol, a propylene glycol, glycerol, and the like, or a mixture of one or more of these non-aqueous solvents with water.

In some embodiments, a preservative is absent (i.e., preservative-free or an absence of preservative). In some embodiments, a preservative is present (i.e., a presence of preservative). In some embodiments, excipient is present (i.e., there is a presence of excipient). In some embodiments, excipient is absent (i.e., an absence of excipient).

The invention also provides a pharmaceutical composition as defined herein, wherein the unit dosage form is liquid. In some embodiments, the liquid unit dosage form is a mixture selected from the group consisting of a solution, a suspension, a dispersion and an emulsion.

The invention also provides a pharmaceutical composition as defined herein, wherein the unit dosage form is solid. In some embodiments, the solid unit dosage form is a lyophilized powder. In some embodiments, the solid unit dosage form is a quick dissolve strip or tablet. In some embodiments, it's a fast melt strip or tablet.

The invention also provides a process for the preparation of the pharmaceutical composition of the invention. The process comprises:
  (a) mixing an alkylammonium salt of R-ibuprofen, S-ibuprofen or R,S-ibuprofen that is capable of complexing with aluminum with an aqueous or a non-aqueous solvent;
  (b) optionally adjusting the pH of mixture (a) to about 7.0 with sodium hydroxide or hydrochloric acid;
  (c) filtering mixture (a) or (b) as the case may be;
  (d) aseptically processing filtered mixture (c) while placing it in an environment for keeping;
  (e) sealing the environment for keeping; and
  (f) optionally terminally sterilizing.

The pharmaceutical composition of the invention also can be made by processes known in the art for preparing ibuprofen alkylammonium salts. See e.g., U.S. Pat. Nos. 4,279,926, 5,895,789 and 6,342,530.

The invention also provides a pharmaceutical composition comprising:
  (a) an alkylammonium salt of R-ibuprofen, S-ibuprofen or R,S-ibuprofen that is capable of complexing with aluminum; and
  (b) an aqueous or a non-aqueous solvent; wherein:
the composition is:
  (a) in unit dosage form in an environment for keeping;
  (b) preservative-free or in a presence of an excipient; and
  (c) substantially-free of ibuprofen aluminum salt precipitate;
prepared by a process comprising the steps:
  (a) mixing an alkylammonium salt of R-ibuprofen, S-ibuprofen or R,S-ibuprofen that is capable of complexing with aluminum compounds with an aqueous solution, suspension or emulsion, or a non-aqueous solution, suspension or emulsion;
  (b) optionally adjusting the pH of mixture (a) to about 7.0 with sodium hydroxide or hydrochloric acid;
  (c) filtering mixture (a) or (b) as the case may be;
  (d) aseptically processing filtered mixture (c) while placing it in an environment for keeping;
  (e) sealing the environment for keeping; and
  (f) optionally terminally sterilizing.

The invention also provides a pharmaceutical composition comprising:
  l) an an alkylammonium salt of ibuprofen selected from the group consisting of R-ibuprofen, S-Ibuprofen and R,S-ibuprofen that is capable of complexing with aluminum;
  m) an aqueous, or a non-aqueous solvent;
  n) optionally an absence of a preservative;
  o) optionally a presence of excipient; and
  p) a substantial absence of ibuprofen aluminum salt precipitate;
wherein the composition is in a unit dosage form in an environment for keeping;
prepared by a process comprising the steps:
  q) mixing an alkylammonium salt of R-ibuprofen, S-ibuprofen or R,S-ibuprofen that is capable of complexing with aluminum compounds with an aqueous solution, suspension or emulsion, or a non-aqueous solution, suspension or emulsion;
  r) optionally adjusting the pH of mixture (a) to about 7.0 with sodium hydroxide or hydrochloric acid;
  s) filtering mixture (a) or (b) as the case may be;
  t) aseptically processing filtered mixture (c) while placing it in an environment for keeping;
  u) sealing the environment for keeping; and
  v) optionally terminally sterilizing.

In some embodiments, the pharmaceutical composition is administered parenterally, such as intravenously. In some embodiments, the pharmaceutical composition is administered orally, such as buccally and sublingually.

The following examples are meant to illustrate the invention without in any way limiting it.

EXAMPLE 1

Aluminum Content in Ibuprofen Lysine Solution

Total aluminum content was measured in multiple batches of Ibuprofen Lysine Solution (i.e., pharmaceutical composition) in Wheaton Type 1 glass vials stored at 25° C. and 60% relative humidity (RH). The aluminum content was measured using inductively coupled plasma mass spectrometry (ICP-MS). The ICP-MS methodology used is well known by those skilled in the art, and it was validated with a limit of quantification (LOQ) of 9 ppb (9 µg/L) established. The ICP-MS method measured the total amount of aluminum present in the vial, i.e., soluble and insoluble. Table 1 shows the storage time of a batch at the time of analysis and the aluminum content measured. The gradual increase in aluminum content over time suggests that the aluminum is continuously being extracted from the inner surface of the vial.

TABLE 1

Aluminum Content in Various Batches of Ibuprofen Lysine Solution

| Batch | Storage Time (months) | Aluminum Content (µg/L) |
| --- | --- | --- |
| 1 | 65 | 112 |
| 2 | 52 | 141 |
| 3 | 34 | 98 |
| 4 | 25 | 108 |
| 5 | 17 | 26 |
| 6 | 14 | 71 |

EXAMPLE 2

Aluminum Content in Ibuprofen Lysine Active

Aluminum content in multiple lots of Ibuprofen Lysine active was measured using inductively coupled plasma mass spectrometry (ICP-MS) method of Example 1 to estimate the aluminum content contribution from the ibuprofen lysine active to formation of an ibuprofen aluminum salt precipitate in the Ibuprofen Lysine solutions of Example 1 and others. The Ibuprofen Lysine active was prepared in water at a concentration of 17 mg/mL, which is the same concentration of the Ibuprofen Lysine solution. As can be seen from the results in Table 2, the contribution from the ibuprofen lysine active to the formation of the ibuprofen aluminum salt precipitate is negligible. Therefore, the ibuprofen lysine active is not a significant source of aluminum in the Ibuprofen Lysine solution.

TABLE 2

Aluminum Content in Various Lots of Ibuprofen Lysine Active

| Batch | Lot Ref. | Aluminum Content µg/g* | µg/L |
| --- | --- | --- | --- |
| 1 | A | 0.18 | <9 |
| 2 | B | 0.32 | <9 |
| 3 | C | 0.15 | <9 |
| 4 | D | 0.18 | <9 |
| 5 | D | 0.18 | <9 |
| 6 | D + E | 0.25** | <9 |
| 7 | E | 0.32 | <9 |
| 8 | F | 0.21 | <9 |

*µg of aluminum per gram of Ibuprofen Lysine.
**value average of Lots D and E individually measured values.

EXAMPLE 3

Accelerating Visible Ibuprofen Aluminum Salt Particulate Formation

Three different concentrations of Ibuprofen Lysine in water were prepared (1.7 mg/mL, 17 mg/mL and 170 mg/mL). The equivalent Ibuprofen concentrations are 1.0 mg/mL, 10 mg/mL and 100 mg/mL, respectively. The solutions were filtered through a 0.2 µm filter, filled into clear borosilicate glass vials commonly used for such solutions (Type I, Wheaton Science Packaging, a division of Wheaton Industries, Inc., Millville, N.J., U.S.A.). The fill volumes were 1 mL, 2 mL and 3 mL for each concentration. The vials were stoppered with a commonly used stopper (Dalkyo Fluorotec® (D777-1 S2-451), West Pharmaceutical Services, Lionville, Pa., U.S.A.) and capped. The filled vials were stored at 25° C., 60° C. and 90° C. and 60% relative humidity. The higher temperature conditions were used to accelerate the effect one would likely observe over a longer period of time at ambient temperature. This practice, with these conditions, often is used in the pharmaceutical art to determine feasibly of long term storage conditions in a shorter than actual period of time. Over a 4-week period, one vial from each condition was visually inspected 2× per week for visible particulate appearance and solution color. The vials were inspected in a light box and observations recorded. The same vial was observed each time for consistency over the 4-weeks. A sample was drawn weekly over the 4-weeks from one vial of each type and the sample tested for aluminum content using inductively coupled plasma mass spectrometry (ICP-MS). The ICP-MS methodology used is well known by those skilled in the art.

As can be seen from the results in Tables 3-4, the 17 mg/mL solution samples stored at 60° C. for 2-weeks produced visible particulate matter with no change in the color of the solution. This finding suggests that a 17 mg/mL Ibuprofen Lysine solution stored for 14 days at 60° C. produces an ibuprofen aluminum salt precipitate. A higher concentration solution (170 mg/mL) at 60° C. or 90° C. produced visible particulate matter, but a change in solution color also was observed, which most probably was due to the formation of degradation products.

Also, the total aluminum content results presented in Table 5 show an increase in aluminum content as a function of both temperature and solution concentration. The amount of aluminum extracted is highest for the most concentrated solution stored at 90° C. Moderate amounts of aluminum were extracted with the 17 mg/mL solution at 60° C.

TABLE 3

Visible Particulate Matter Results[1]

| Conc. (mg/mL) | Temp. (°C.) | Fill Vol. (mL) | 7 days | 14 days | 21 days | 28 days |
| --- | --- | --- | --- | --- | --- | --- |
| 1.7 | 25 | 1 | None | None | Yes | Fiber |
|  |  | 2 | None | Fiber | Fiber | Fiber |
|  |  | 3 | None | None | Fiber | Fiber |
|  | 60 | 1 | None | Yes | Fiber | Fiber |
|  |  | 2 | None | Fiber | Fiber | Fiber |
|  |  | 3 | None | Fiber | Fiber | Fiber |
|  | 90 | 1 | None | Yes | Fiber | Fiber |
|  |  | 2 | None | Yes | Fiber | Fiber |
|  |  | 3 | None | Yes | Fiber | Fiber |
|  | 25 | 1 | None | None | Fiber | Fiber |
|  |  | 2 | None | Fiber | Fiber | Fiber |
|  |  | 3 | None | None | None | Fiber |

TABLE 3-continued

Visible Particulate Matter Results[1]

| Conc. (mg/mL) | Temp. (°C.) | Fill Vol. (mL) | 7 days | 14 days | 21 days | 28 days |
|---|---|---|---|---|---|---|
| 17 | 60 | 1 | None | Yes | Yes | Yes |
|  |  | 2 | None | Yes | Yes | Yes |
|  |  | 3 | None | Yes | Fiber | Yes |
|  | 90 | 1 | Yes | Yes | Yes | Yes |
|  |  | 2 | Yes | Yes | Yes | Yes |
|  |  | 3 | Yes | Yes | Yes | Yes |
|  | 25 | 1 | None | Fiber | Yes | Fiber |
|  |  | 2 | None | Fiber | Fiber | Fiber |
|  |  | 3 | None | Fiber | Yes | Fiber |
| 170 | 60 | 1 | None | Yes | Yes | Yes |
|  |  | 2 | None | Yes | Yes | Yes |
|  |  | 3 | None | Yes | Yes | Yes |
|  | 90 | 1 | None | Yes | Yes | Yes |
|  |  | 2 | None | Yes | Yes | Yes |
|  |  | 3 | None | Yes | Yes | Yes |

[1]Yes = particulates visible, i.e., precipitate found; Fiber = fiber-like particulates observed, i.e., precipitate found.

TABLE 4

Solution Color Results

| Conc. (mg/mL) | Temp. (° C.) | Fill Vol. (mL) | 7 days | 14 days | 21 days | 28 days |
|---|---|---|---|---|---|---|
| 1.7 | 25 | 1 | Colorless | Colorless | Colorless | Colorless |
|  |  | 2 | Colorless | Colorless | Colorless | Colorless |
|  |  | 3 | Colorless | Colorless | Colorless | Colorless |
|  | 60 | 1 | Colorless | Colorless | Colorless | Colorless |
|  |  | 2 | Colorless | Colorless | Colorless | Colorless |
|  |  | 3 | Colorless | Colorless | Colorless | Colorless |
|  | 90 | 1 | Colorless | Colorless | Colorless | Colorless |
|  |  | 2 | Colorless | Colorless | Colorless | Colorless |
|  |  | 3 | Colorless | Colorless | Colorless | Colorless |
| 17 | 25 | 1 | Colorless | Colorless | Colorless | Colorless |
|  |  | 2 | Colorless | Colorless | Colorless | Colorless |
|  |  | 3 | Colorless | Colorless | Colorless | Colorless |
|  | 60 | 1 | Colorless | Colorless | Colorless | Colorless |
|  |  | 2 | Colorless | Colorless | Colorless | Colorless |
|  |  | 3 | Colorless | Colorless | Colorless | Colorless |
|  | 90 | 1 | Pale Yellow | Pale Yellow | Pale Yellow | Pale Yellow |
|  |  | 2 | Pale Yellow | Pale Yellow | Pale Yellow | Pale Yellow |
|  |  | 3 | Pale Yellow | Pale Yellow | Pale Yellow | Pale Yellow |
| 170 | 25 | 1 | Colorless | Colorless | Colorless | Pale Yellow |
|  |  | 2 | Colorless | Colorless | Colorless | Pale Yellow |
|  |  | 3 | Colorless | Colorless | Colorless | Pale Yellow |
|  | 60 | 1 | Pale Yellow | Yellow | Yellow | Yellow |
|  |  | 2 | Pale Yellow | Yellow | Yellow | Yellow |
|  |  | 3 | Pale Yellow | Yellow | Yellow | Yellow |
|  | 90 | 1 | Yellow | Dark Yellow | Dark Yellow | Dark Yellow |
|  |  | 2 | Yellow | Dark Yellow | Dark Yellow | Dark Yellow |
|  |  | 3 | Yellow | Yellow | Dark Yellow | Dark Yellow |

TABLE 5

Aluminum Content Results

| Conc. (mg/mL) | Temp. (° C.) | Fill Vol. (mL) | Aluminum Content (µg/L) | | | |
|---|---|---|---|---|---|---|
|  |  |  | 7 days | 14 days | 21 days | 28 days |
| 1.7 | 25 | 1 | 11 | 5 | 5 | 12 |
|  |  | 2 | 17 | 2 | 6 | 3 |
|  |  | 3 | 5 | 3 | 1 | 13 |
|  | 60 | 1 | 10 | 7 | 6 | 15 |
|  |  | 2 | 5 | 8 | 17 | 11 |
|  |  | 3 | 4 | 4 | 7 | 18 |
|  | 90 | 1 | 408 | 100 | Not Tested | 33 |
|  |  | 2 | 59 | 81 | 15 | 7 |
|  |  | 3 | 70 | 36 | 32 | 24 |
| 17 | 25 | 1 | 14 | 8 | 11 | 11 |
|  |  | 2 | 6 | 3 | 5 | 6 |
|  |  | 3 | 8 | 13 | 4 | 2 |
|  | 60 | 1 | 18 | 28 | 38 | 52 |
|  |  | 2 | 13 | 19 | 23 | 12 |
|  |  | 3 | 11 | 11 | 20 | 9 |
|  | 90 | 1 | 28 | 21 | 33 | 34 |
|  |  | 2 | 14 | 12 | 17 | 23 |
|  |  | 3 | 6 | 14 | 15 | 22 |
| 170 | 25 | 1 | 17 | 33 | 35 | 38 |
|  |  | 2 | 14 | 125 | 19 | 21 |
|  |  | 3 | 25 | 31 | 15 | 39 |
|  | 60 | 1 | 50 | 61 | 64 | 84 |
|  |  | 2 | 60 | 20 | 104 | 160 |
|  |  | 3 | 59 | 83 | 80 | 153 |
|  | 90 | 1 | 301 | 405 | 316 | 276 |
|  |  | 2 | 416 | 435 | 388 | 731 |
|  |  | 3 | 286 | 328 | 312 | 472 |

EXAMPLE 4

Determination of Visible Precipitate from Example 3

Figure 1:
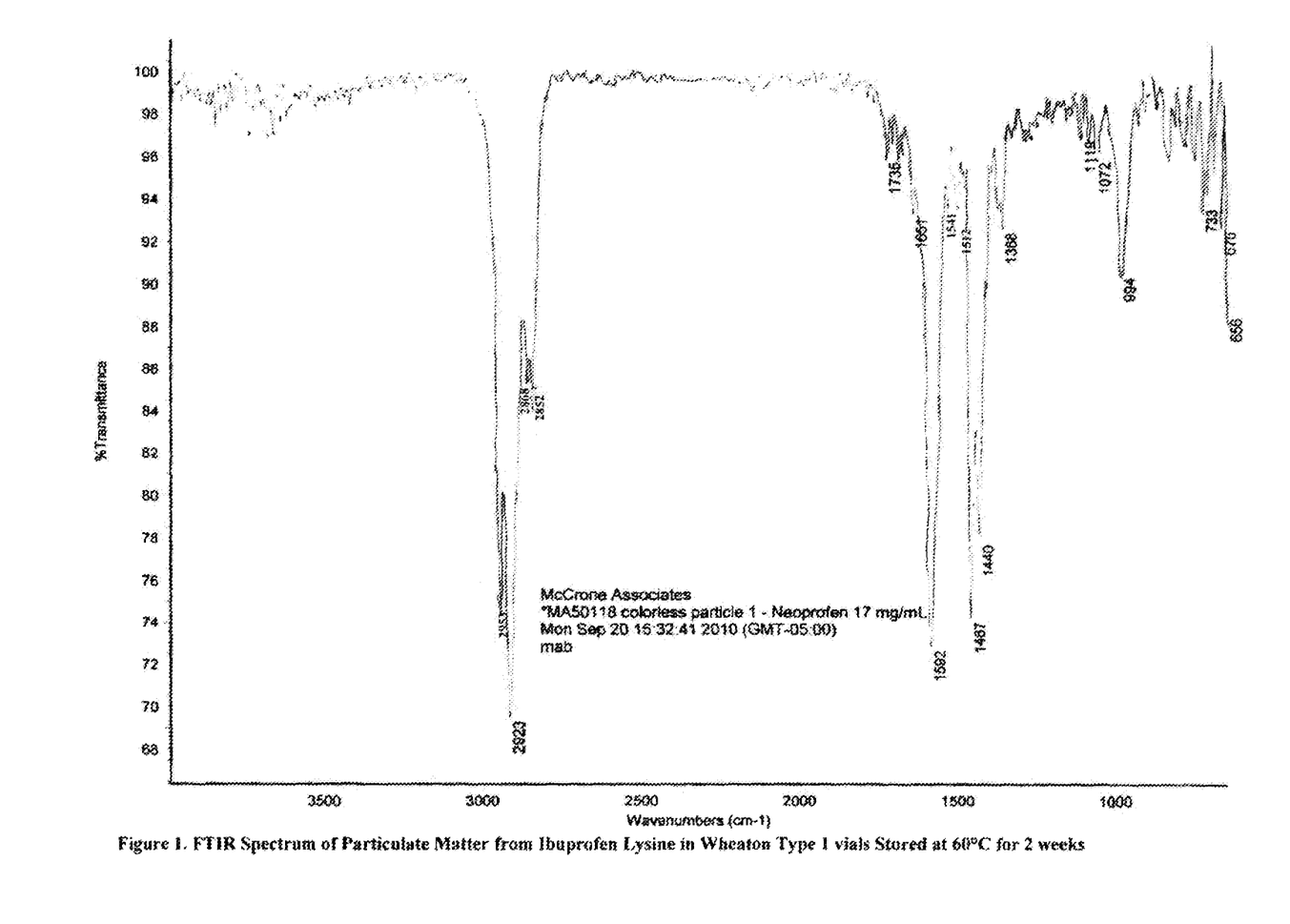
FIG. 1: FTIR spectrum of particulate matter from a representative ibuprofen lysine solution.
Figure 2:
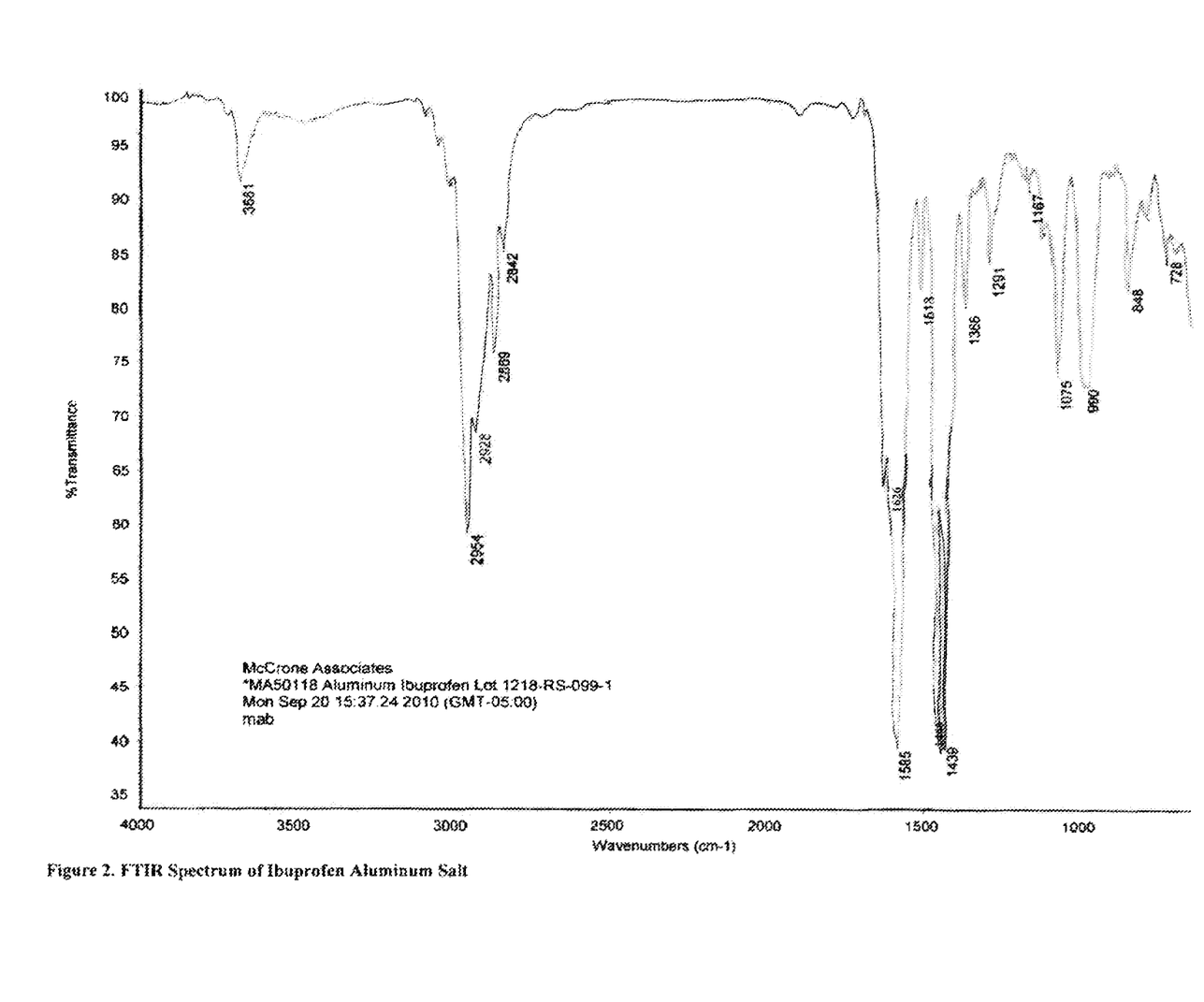
FIG. 2: FTIR spectrum of a representative aluminum ibuprofen salt.

To determine whether the observed particulate material in the 17 mg/mL Ibuprofen Lysine solution stored for 14 days at 60° C. in EXAMPLE 2 was ibuprofen aluminum salt, the particulate matter was tested by Fourier transform infrared (FTIR) spectroscopy. Aluminum salts of ibuprofen (1:1, 2:1 and 3:1) were synthesized as described by Fitch and Rowe in U.S. Pat. No. 4,145,440. The FTIR results for the precipitate from EXAMPLE 2 (see e.g., FIG. 1) are reasonably identical to the FTIR spectrum obtained for the ibuprofen aluminum salts (see e.g., FIG. 2), thereby confirming that the particulate matter was ibuprofen aluminum salt precipitate.

EXAMPLE 5

Aluminum Extraction from Various Types of Vials

Three different brands of vials were evaluated for aluminum extraction by rinsing each vial with three 3-mL aliquots (total 9-mL) of 10% v/v hydrochloric acid and the rinse solution was analyzed for aluminum content using inductively coupled plasma (ICP). As can be seen from the results in Table 6, aluminum was extracted from the commonly used Wheaton Type 1 vial, but not from vials having an inert atmosphere to the ibuprofen lysine contained within it—namely, the Schott Type I Plus® vials and the Dalkyo Crystal Zenith® vials.

TABLE 6

Aluminum content extracted from various type of vials

| Vial Type | Preparation # | Aluminum Content (µg) |
|---|---|---|
| Wheaton | 1 | 0.1 |
| Type I | 2 | 0.1 |
|  | 3 | 0.2 |
| Schott | 1 | 0.0 |
| Type I | 2 | 0.0 |
| plus ® | 3 | 0.0 |
| Daikyo | 1 | 0.0 |
| Crystal | 2 | 0.0 |
| Zenith ® | 3 | 0.0 |

EXAMPLE 6

Formation of Ibuprofen Aluminum Salt from Uncoated and Coated Glass Vials

Figure 3:
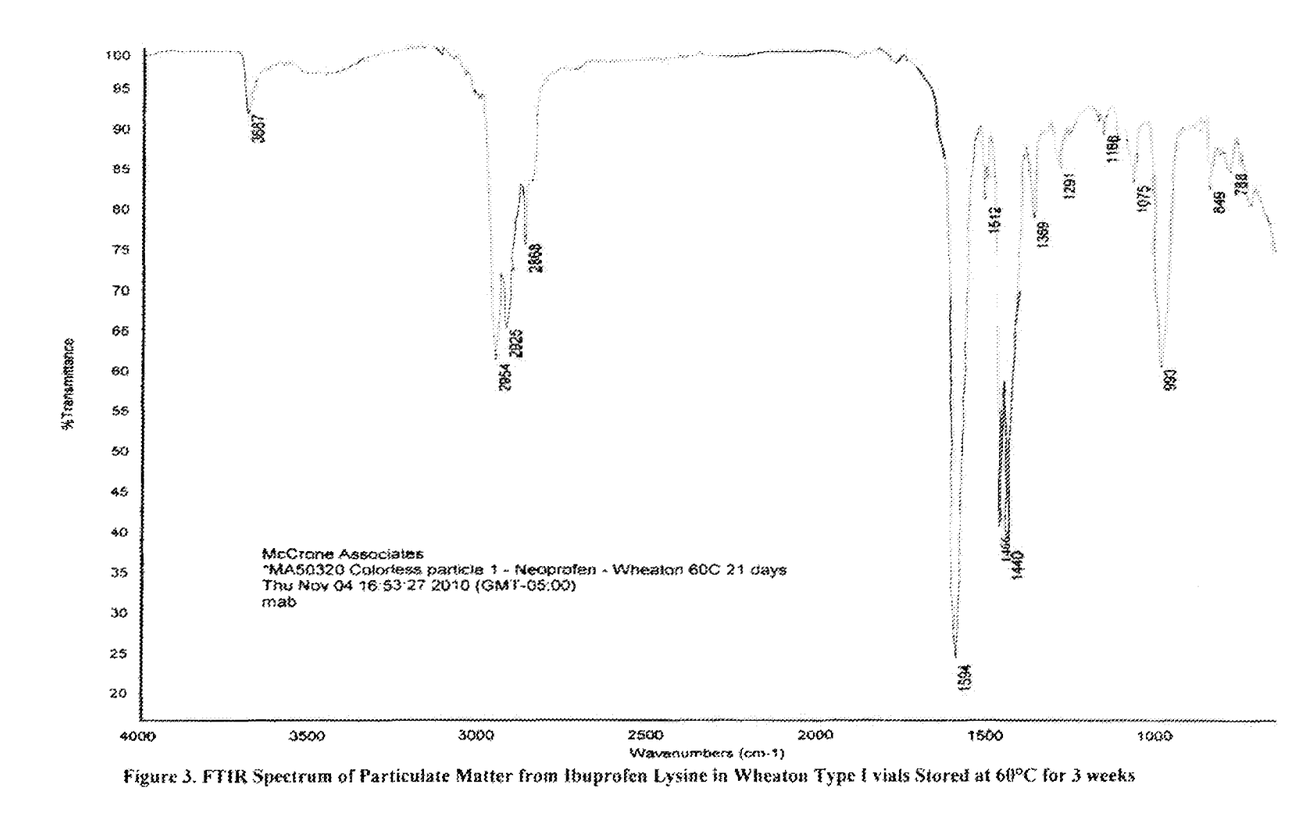
FIG. 3: FTIR spectrum of particulate matter from a representative ibuprofen lysine solution.

Ibuprofen Lysine solution in water was prepared at a concentration of 17 mg/mL (equivalent to Ibuprofen concentration of 10 mg/mL). The solution was filtered through a 0.2 µm filter and filled into Wheaton Type 1 vials and Schott Type I Plus® vials at a fill volume of 2 mL. The vials were stoppered with the Dalkyo D777-1 S2-451 Fluorotec® stoppers and capped. The vials were stored at 60° C. in the upright position. Samples were drawn weekly over a 4-week period and tested for visible particulate appearance, solution color and aluminum content using ICP-MS. As can be seen from Table 7, this study confirmed that the ibuprofen aluminum salt precipitate forms in the Wheaton vials and fails to form in the Schott Type I Plus® vials. Samples stored for 3-weeks at 60° C. also were tested for particulate identification by FTIR, which confirmed the precipitate was ibuprofen aluminum salt. (compare FIG. 3 with FIGS. 1-2).

TABLE 7

Ibuprofen aluminum salt formation in two types of vials stored at 60° C.

| Test | Vial | Time (days) | | | | |
|---|---|---|---|---|---|---|
| | | 0 | 7 | 14 | 21 | 28 |
| Visible Particulate Matter | Wheaton Type I | None | May be | Yes | Large Particulates | Large Particulates |
| | Schott Type I plus ® | None | May be | One Particulate | Yes | Yes |
| Solution Color | Wheaton Type I | Colorless | Colorless | Colorless | Colorless | Colorless |
| | Schott Type I plus ® | Colorless | Colorless | Colorless | Colorless | Colorless |
| Aluminum Content (µg/L) | Wheaton Type I | <3 | 3 | 3 | 11 | 14 |
| | Schott Type I plus ® | <3 | 6 | <3 | 9 | 11 |

EXAMPLE 7

Vial Interior Surface Characterization

The interior surface of Schott Type I Plus® and commonly used Wheaton vials were characterized for elemental content. Samples of empty, unused vials were broken open in an ISO Class V clean room and the interior surfaces of the vials were examined by light microscopy, scanning electron microscopy (SEM) and X-ray photoelectron spectroscopy (XPS).

Figure 4:
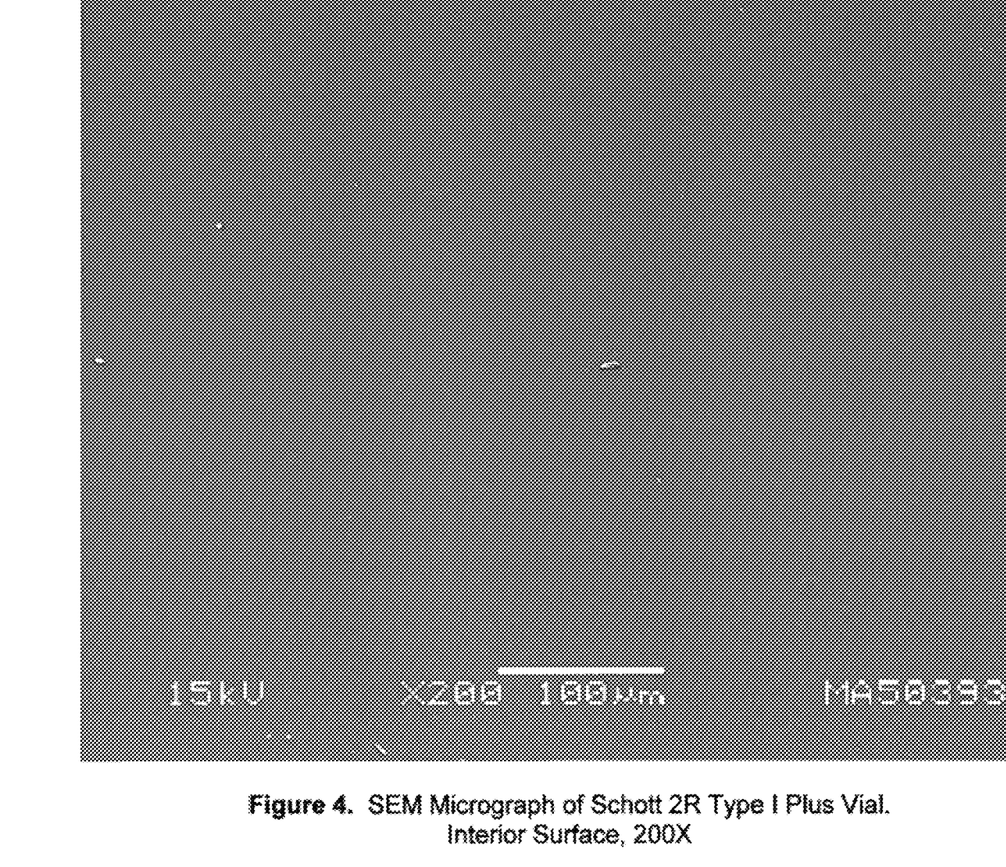
FIG. 4: SEM monograph of the interior surface of a representative vial having an inert interior coating.
Figure 5:
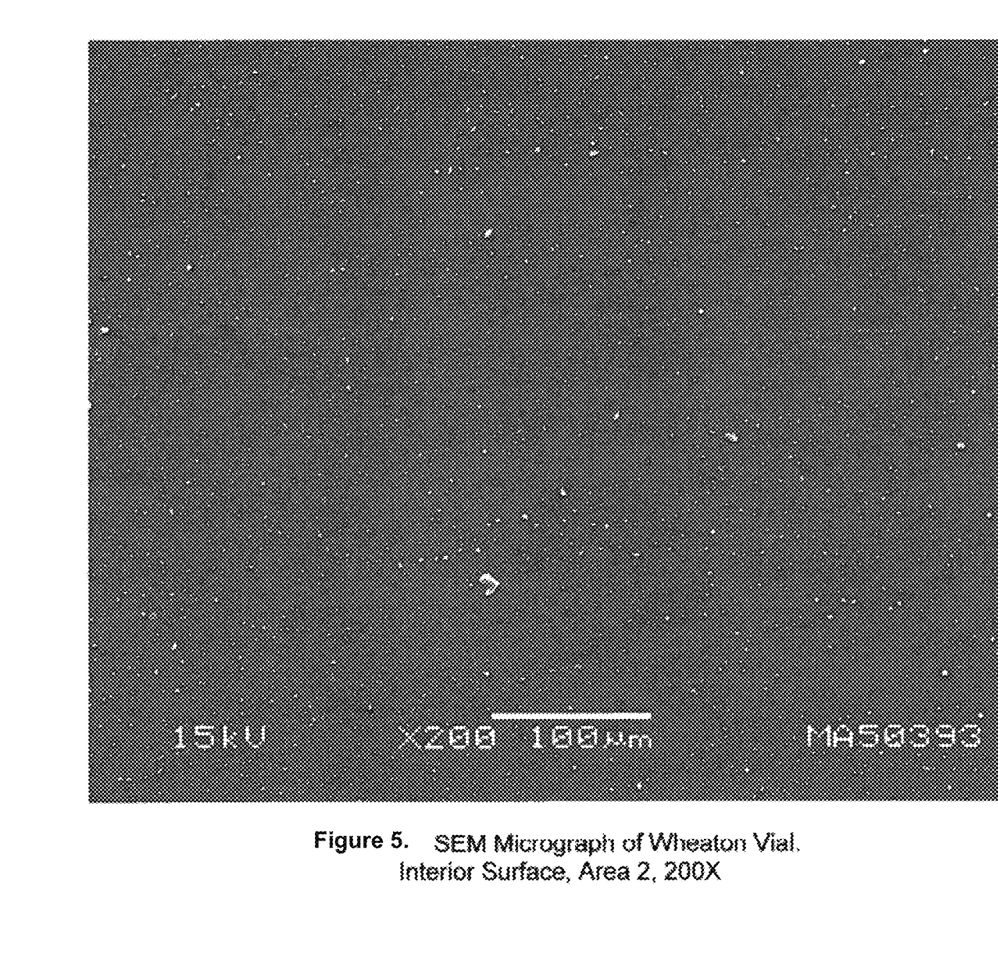
FIG. 5: SEM monograph of the interior surface of a representative vial lacking an inert interior coating.

Conclusions from this study are that the Schott Type I Plus® vials have clean interior surfaces with a thin surface coating consistent with $SiO_2$. Defect spots on the interior surface were very rare. The interior surface showed no pitting, delamination or other signs of degradation. See e.g., FIG. 4. The Wheaton vials had extensive degradation with delamination, deposits and possible pitting. Some of the deposits contained sodium and sulfur. The degradation was most extensive near the base of the vials. See e.g., FIG. 5.

As can be seen from the results of the XPS analysis in Table 8, there is a presence of aluminum in the interior surfaces of the Wheaton Type I vials while there is an absence of aluminum in the interior surfaces of the Schott Type I Plus® vials.

TABLE 8

XPS analysis results for interior surface of two vial types[2]

| Vial Type | Atomic Percentage | | | | | | |
|---|---|---|---|---|---|---|---|
| | Oxygen | Silicon | Carbon | Sodium | Boron | Aluminum | Sulfur |
| Schott Type I plus ® | 69.1 ±0.2 | 27.5 ±0.14 | 2.9 ±0.3 | nd — | nd — | nd — | nd — |
| Wheaton Type I | 66.2 ±0.4 | 22.7 ±0.4 | 3.3 ±0.4 | 2.4 ±0.4 | 4.5 ±0.5 | 0.45 ±0.03 | 0.55 ±0.08 |

[2]Average of six measurements ± one standard deviation;
nd = not detected (<0.2-1.0 atomic %).

EXAMPLE 8

Ibuprofen Lysine Solution in an Environment Substantially Inert to Formation of Ibuprofen Aluminum Salt Three batches of Ibuprofen Lysine solution kept in Schott Type I Plus® vials with the Dalkyo D777-1 S2-451 Fluorotec® stoppers and caps were evaluated for formation of ibuprofen aluminum salt. The solution was prepared so that each milliliter (mL) of solution contains 17.1 mg of Ibuprofen Lysine (equivalent to 10 mg of (±)-ibuprofen) in Water for Injection, USP. The vials were stored at 25° C./60% RH and 40° C./75% RH in upright and inverted positions. Particulate matter, particulate identification and aluminum content was monitored. Also, a one-month study at 60° C./60% RH in the upright position was conducted. Particulate identification and aluminum content was measured.

1) Particulate Matter
   a) Light Obscuration

Particulate matter test through light obscuration was conducting according to USP <788>, Particulate Matter in Injections test. The results for particle size ≧10 μm/container for vials stored through 12 months at 25° C./60% RH and through 6 months at 40° C./75% RH are shown in Tables 9 and 10, respectively. The results for particle size ≧10 μm/container for vials stored through 12 months at 25° C./60% RH and through 6 months at 40° C./75% RH are in Tables 9 and 10, respectively. The results for particle size ≧25 μm/container for vials stored through 12 months at 25° C./60% RH and through 6 months at 40° C./75% RH are in Tables 11 and 12, respectively. These results show no change in particulate matter at 25° C./60% RH and 40° C./75% RH storage conditions over time regardless of the vial position orientation.

TABLE 9

Particulate Matter ≧10 μm at 25° C./60% RH Results

| Batch # | Orientation | Particulate Matter Count ≧10 μm/vial | | | | | | |
|---|---|---|---|---|---|---|---|---|
| | | 0 | 1 mon | 2 mon | 3 mon | 6 mon | 9 mon | 12 mon |
| 2A | upright | 152 | 99 | 104 | 84 | 56 | 116 | 145 |
| | inverted | | 68 | 146 | 117 | 88 | 170 | 213 |
| 2B | upright | 62 | 56 | 79 | 54 | 29 | 42 | 57 |
| | inverted | | 57 | 105 | 104 | 68 | 176 | 124 |
| 2C | upright | 116 | 62 | 88 | 160 | 26 | 72 | 75 |
| | inverted | | 58 | 138 | 167 | 39 | 145 | 160 |

TABLE 10

Particulate Matter ≧10 μm at 40° C./75% RH Results

| Batch # | Orientation | Particulate Matter Count ≧10 μm/vial | | | | |
|---|---|---|---|---|---|---|
| | | 0 | 1 mon | 2 mon | 3 mon | 6 mon |
| 2A | upright | 152 | 65 | 80 | 102 | 92 |
| | inverted | | 93 | 133 | 113 | 30 |
| 2B | upright | 62 | 54 | 48 | 35 | 58 |
| | inverted | | 54 | 91 | 86 | 24 |
| 2C | upright | 116 | 54 | 67 | 106 | 58 |
| | inverted | | 90 | 90 | 89 | 28 |

TABLE 11

Particulate Matter ≧25 μm at 25° C./60% RH Results

| Batch # | Orientation | Particulate Matter Count ≧25 μm/vial | | | | | | |
|---|---|---|---|---|---|---|---|---|
| | | 0 | 1 mon | 2 mon | 3 mon | 6 mon | 9 mon | 12 mon |
| 2A | Upright | 4 | 3 | 5 | 3 | 3 | 4 | 6 |
| | inverted | | 4 | 8 | 6 | 3 | 8 | 10 |
| 2B | Upright | 2 | 1 | 2 | 3 | 1 | 1 | 2 |
| | inverted | | 2 | 4 | 3 | 2 | 6 | 6 |
| 2C | Upright | 4 | 2 | 4 | 8 | 0 | 4 | 4 |
| | inverted | | 2 | 6 | 6 | 2 | 6 | 8 |

TABLE 12

Particulate Matter ≧25 μm at 40° C./75% RH Results

| Batch # | Orientation | Particulate Matter Count ≧25 μm/vial | | | | |
|---|---|---|---|---|---|---|
| | | 0 | 1 mon | 2 mon | 3 mon | 6 mon |
| 2A | upright | 4 | 3 | 3 | 4 | 3 |
| | inverted | | 4 | 6 | 5 | 2 |
| 2B | upright | 2 | 2 | 1 | 1 | 2 |
| | inverted | | 1 | 4 | 2 | 0 |
| 2C | upright | 4 | 3 | 2 | 3 | 1 |
| | inverted | | 4 | 2 | 2 | 0 | b) Optical Microscopy

Particulate matter was also detected by optical microscopy. The methodology is well know by those skilled in the art and also is known as Light Microscopy. All particle sizes were below 60 μm, which is well below the visible particulate matter detection limit of approximately 100 μm.

2) Particulate Identification

The particulate matter determined by optical microscopy was collected and then identified by infrared (IR) spectroscopy. The methodology used is well known to those skilled in the art. Tables 13-15 show the results of ibuprofen aluminum salt by IR spectroscopy detection. These results show no ibuprofen aluminum salt formation after 12 months of storage at 25° C./60% RH. At 40° C./75% RH, there is some inconsistency in the detection of ibuprofen aluminum salt as detected at 2 and 6 month time points and not at the 3 month time point. This may be due to the very low amount of ibuprofen aluminum salt formed at the 40° C./75% RH storage condition as shown in Table 17. Ibuprofen aluminum salt formed at the 60° C./60% RH, 1 month, storage condition. See also Table 18.

TABLE 13

Ibuprofen Aluminum Salt Detection at 25° C./60% RH

| Batch # | Orientation | Time | | | |
|---|---|---|---|---|---|
| | | 3 months | 6 months | 9 months | 12 months |
| 2A | upright | None present | None present | None present | None present |
| 2B | upright | None present | None present | None present | None present |
| 2C | upright | None present | None present | None present | None present |

TABLE 14

Ibuprofen Aluminum Salt Detection at 40° C./75% RH

| Batch # | Orientation | Time | | |
|---|---|---|---|---|
| | | 2 months | 3 months | 6 months |
| 2A | upright | Present | None present | Present |
| 2B | upright | Present | None present | Present |
| 2C | upright | Present | None present | Present |

TABLE 15

Ibuprofen Aluminum Salt Detection at 60° C./60% RH

| Batch # | Orientation | Time 1 month |
|---|---|---|
| Control | Upright | Present |
| 2A | upright | Present |
| 2B | upright | Present |
| 2C | upright | Present |

*Control in Wheaton Type I vial.

Aluminum Content

Aluminum content was determined using the ICP-MS disclosed herein. An Ibuprofen Lysine solution kept in the Wheaton Type 1 vial of approximately 9 months old was used as a control for the samples tested at the 40° C./75% RH and 60° C./60% RH storage conditions. As can be seen from the results in Tables 16-18, there was no substantial change in aluminum content for all tested conditions, while there was a substantial increase in aluminum content in the control by 1 month at 40° C./75% RH and 7 days at 60° C./60% RH. This aluminum content continued to increase over time. Consequently, the tested Ibuprofen Lysine solution is substantially-free of ibuprofen aluminum salt.

TABLE 16

Total Aluminum Content Results at 25° C./60% RH

| Batch # | Orientation | Aluminum Content (μg/L) | | | | | |
|---|---|---|---|---|---|---|---|
| | | 0 | 1 mon | 2 mon | 3 mon | 6 mon | 9 mon |
| 2A | upright | 13 | <9 | <9 | <9 | 57 | <9 |
| | inverted | | <9 | <9 | <9 | <9 | <9 |
| 2B | upright | 12 | 18 | <9 | <9 | <9 | <9 |
| | inverted | | <9 | 52 | <9 | <9 | <9 |
| 2C | upright | <9 | <9 | <9 | <9 | <9 | <9 |
| | inverted | | 12 | <9 | <9 | 9 | <9 |

TABLE 17

Total Aluminum Content Results 40° C./75% RH

| Batch # | Orientation | Aluminum Content (μg/L) | | | | |
|---|---|---|---|---|---|---|
| | | 0 | 1 mon | 2 mon | 3 mon | 6 mon |
| Control* | upright | 45 | 137 | 163 | 207 | 311 |
| 2A | upright | 13 | <9 | <9 | <9 | 22 |
| | inverted | | <9 | <9 | 17 | <9 |
| 2B | upright | 12 | <9 | 13 | <9 | 92 |
| | inverted | | <9 | <9 | <9 | 45 |
| 2C | upright | <9 | <9 | 66 | <9 | 28 |
| | inverted | | <9 | <9 | <9 | <9 |

*Control in Wheaton Type I vial

TABLE 18

Total Aluminum Content Results at 60° C./60% RH

| Batch # | Orientation | Aluminum Content (μg/L) | | | | |
|---|---|---|---|---|---|---|
| | | 0 | 7 days | 14 days | 21 days | 1 mon |
| Control* | upright | 45 | 198 | 247 | 230 | 165 |
| 2A | upright | <9 | <9 | 14 | 34 | 49 |
| 2B | upright | <9 | <9 | 26 | 36 | 63 |
| 2C | upright | <9 | <9 | 24 | 38 | 52 |

*Control in Wheaton Type I vial

What is claimed is:

1. A pharmaceutical composition comprising:
a) an alkylammonium salt of ibuprofen selected from the group consisting of R ibuprofen, S-Ibuprofen and R,S-ibuprofen;
b) an aqueous, or a non-aqueous solvent;
c) optionally an absence of preservative- and
d) optionally the presence of an excipient; wherein:
the composition is in a unit dosage form in a vial, ampoule, blister pack or prefillable delivery system, said vial, ampoule, blister pack or prefillable delivery system comprises glass having a silicon dioxide coating or polymer coating disposed on the inner wall.

2. The pharmaceutical composition of claim 1, wherein the composition can be administered parenterally.

3. The pharmaceutical composition of claim 1, wherein there is an absence of preservative.

4. The pharmaceutical composition of 1, wherein there is a presence of excipient.

5. The pharmaceutical composition of claim 1, where in the environment for keeping is inert such that the pharmaceutical composition has less than about 5 μg/L of ibuprofen aluminum salt precipitate.

6. A pharmaceutical composition of claim 1, wherein the composition is in a vial and the polymer coating is comprised of Teflon®.

7. The pharmaceutical composition of claim 1, wherein the composition is in a vial and the coating is comprised of silicon dioxide.

8. The pharmaceutical composition of claim 1, wherein the liquid unit dosage form is a mixture selected from the group consisting of a solution, suspension, dispersion and emulsion.

9. The pharmaceutical composition of claim 1, wherein the alkylammonium salt is selected from a group consisting of d,l-lysine, l-lysine, d-lysine, tromethamine, and meglumine.

10. The pharmaceutical composition of claim 1, wherein the alkylammonium salt is selected from the group consisting of d,l-lysine, l-lysine and d-lysine.

* * * * *